United States Patent
Treskow et al.

(10) Patent No.: US 12,378,183 B2
(45) Date of Patent: Aug. 5, 2025

(54) PROCESS FOR PREPARING GLYCEROL CARBONATE (METH)ACRYLATE

(71) Applicant: Evonik Operations GmbH, Essen (DE)

(72) Inventors: Marcel Treskow, Darmstadt (DE); Günther Gräff, Bensheim (DE); Maik Caspari, Alsbach-Haehnlein (DE); Thorben Schütz, Alsbach-Haehnlein (DE); Steffen Krill, Muehltal (DE)

(73) Assignee: Evonik Operations GmbH, Essen (DE)

( * ) Notice: Subject to any disclaimer, the term of this patent is extended or adjusted under 35 U.S.C. 154(b) by 773 days.

(21) Appl. No.: 17/755,100

(22) PCT Filed: Oct. 2, 2020

(86) PCT No.: PCT/EP2020/077612
§ 371 (c)(1),
(2) Date: Apr. 21, 2022

(87) PCT Pub. No.: WO2021/078492
PCT Pub. Date: Apr. 29, 2021

(65) Prior Publication Data
US 2022/0388943 A1 Dec. 8, 2022

(30) Foreign Application Priority Data
Oct. 23, 2019 (EP) .................................... 19204739

(51) Int. Cl.
*A61K 31/4745* (2006.01)
*A61K 31/4704* (2006.01)
*A61P 35/00* (2006.01)
*C07C 68/06* (2020.01)

(52) U.S. Cl.
CPC .................................... *C07C 68/06* (2013.01)

(58) Field of Classification Search
CPC ............ A61K 31/4745; A61K 31/4704; A61K 45/06; A61K 39/3955; A61K 2300/00; A61P 35/00; C07K 16/2818
See application file for complete search history.

(56) References Cited

U.S. PATENT DOCUMENTS

| 2007/0106044 A1 | 5/2007 | Schmitt et al. |
| 2022/0056005 A9 | 2/2022 | Treskow et al. |

FOREIGN PATENT DOCUMENTS

| DE | 3937116 | 5/1991 |
| WO | 2000/031195 | 6/2000 |
| WO | 2005/058862 | 6/2005 |
| WO | 2017/112881 | 6/2017 |

OTHER PUBLICATIONS

European Search Report dated Feb. 11, 2020 in European Application No. 19204739.7, 5 pages.
International Search Report mailed Nov. 20, 2020 in PCT/EP2020/077612, 5 pages.
Written Opinion mailed Nov. 20, 2020 in PCT/EP2020/077612, 7 pages.
U.S. Appl. No. 16/973,995, filed Dec. 10, 2020, 2022/0056005-A9, Treskow et al.

*Primary Examiner* — Sun Jae Yoo
(74) *Attorney, Agent, or Firm* — Grüneberg and Myers PLLC

(57) ABSTRACT

A process prepares glycerol carbonate (meth)acrylate by transesterification of methyl (meth)acrylate with glycerol carbonate, in the presence of a zirconium acetylacetonate catalyst. The catalyst is pretreated with 2% by weight to 25% by weight of water, based on the amount of catalyst.

20 Claims, No Drawings

PROCESS FOR PREPARING GLYCEROL CARBONATE (METH)ACRYLATE

CROSS-REFERENCE TO RELATED APPLICATIONS

This application is the National Stage entry under § 371 of International Application No. PCT/EP2020/077612, filed on Oct. 2, 2020, and which claims the benefit of priority to European Application No. 19204739.7, filed on Oct. 23, 2019. The content of each of these applications is hereby incorporated by reference in its entirety.

BACKGROUND OF THE INVENTION

Field of the Invention

The invention relates to a process for preparing glycerol carbonate (meth)acrylate from glycerol carbonate and methyl (meth)acrylate using zirconium acetylacetonate as catalyst.

Description of Related Art

In the coatings and adhesives industry, (2-oxo-1,3-dioxolan-4-yl)methyl (meth)acrylate ("glycerol carbonate (meth)acrylate") is a commonly employed resin constituent used for curing or aftertreatment of films.

Various processes for preparing glycerol carbonate methacrylate are already described in the prior art:

In JP 2001018729, glycerol carbonate is reacted with acryloyl chloride. The chloride waste that arises is a substantial environmental burden. In WO 2000/031195, glycidyl methacrylate is reacted with $CO_2$. This process is carried out at high pressure. The process apparatus needed for this is elaborate and costly. In DE 3937116, an alcohol having a cyclic carbonate structure is reacted with a carboxylic acid at elevated temperature and in the presence of an acid catalyst. The desired product is obtained by distillation in a purity of 75.5%. The yield varies between 25.5 and 83%, depending on the acid used. With the purity of only 75.5% achieved here, it is not possible to use the product in many applications.

In the preparation of glycerol carbonate (meth)acrylate from glycerol carbonate and methyl (meth)acrylate in the presence of zirconium acetylacetonate ($Zr(acac)_4$), not only the desired target product, but also unwanted crosslinkers such as glycerol di(meth)acrylate and glycerol tri(meth)acrylate are formed, which at concentrations greater than 2.5% prevent use of the product in coatings or adhesives production.

WO 2005/058862 A2 describes a process for preparing glycerol carbonate methacrylate using zirconium acetylacetonate as catalyst. The reaction is carried out under anhydrous conditions, with the reaction mixture dewatered before addition of the catalyst. This methodology affords glycerol carbonate methacrylate having crosslinker contents of between 1.8% and 2.3%. However, these crosslinker contents are still too high for some applications that are particularly sensitive to crosslinkers, for example in the coatings sector.

It was thus an object of the present invention to provide an improved process for preparing glycerol carbonate (meth)acrylate with which the crosslinker content may be reduced further while still achieving good yields and high product purity. The crosslinker content should be less than 1.5%, ideally less than 1.0%.

SUMMARY OF THE INVENTION

Said object is achieved by a process for preparing glycerol carbonate (meth)acrylate by transesterification of methyl (meth)acrylate with glycerol carbonate in the presence of a zirconium acetylacetonate catalyst, wherein the catalyst is pretreated with 2% by weight to 25% by weight of water, based on the amount of catalyst.

DETAILED DESCRIPTION OF THE INVENTION

In the work underlying the invention, it was surprisingly found that a marked decline in the crosslinkers formed as unwanted by-products is achieved when the preparation of glycerol carbonate (meth)acrylate from glycerol carbonate and methyl (meth)acrylate in the presence of a zirconium acetylacetonate catalyst is accompanied by pretreatment of the catalyst with water (2% by weight to 25% by weight, preferably 8% by weight to 20% by weight and more preferably 9% by weight to 18% by weight, based on the amount of catalyst). Moreover, there is a rise in the purity of the product as a result of this suppression of side reactions. This observation is particularly surprising since not only can the water act as a catalyst poison, it can cause cleavage of the carbonate (ring opening, liberation of glycerol). Optimal selectivity in respect of the absence of crosslinker formation is achieved by $Zr(acac)_4$ at a water concentration of 15% by weight. The substantial reduction in the crosslinker content allows inter alia the use of the product as a resin constituent in coating formulations.

In accordance with the above, the invention relates to a process for preparing glycerol carbonate (meth)acrylate by transesterification of methyl (meth)acrylate with glycerol carbonate in the presence of a zirconium acetylacetonate catalyst, wherein the catalyst is pretreated with 2% by weight to 25% by weight of water, preferably 8% by weight to 20% by weight of water, more preferably 9% by weight to 18% by weight of water, based on the amount of catalyst.

The process according to the invention affords glycerol carbonate (meth)acrylate having a crosslinker content of less than 1.5%.

The pretreatment of the catalyst with water may be carried out directly in the reaction mixture, i.e. in the presence of the reactants methyl (meth)acrylate or glycerol carbonate (and optionally in the presence of at least one stabilizer). The water needed for the pretreatment may be introduced into the reaction mixture for example together with glycerol carbonate. It is however preferable for the pretreatment of the catalyst with water to be carried out before the start of the transesterification and in the presence of only methyl (meth)acrylate (and optional stabilizer), but in the absence of glycerol carbonate.

This pretreatment step may be carried out with heating of the mixture, for example within a temperature range from 70° C. to 110° C.

The transesterification itself commences when the reactants methyl (meth)acrylate and glycerol carbonate are brought into contact. Preferably the reaction mixture is dewatered after pretreatment of the catalyst, but before the start of the transesterification reaction.

In a particular embodiment of the invention, methyl (meth)acrylate, water and optional stabilizers(s) are initially charged and the transesterification is finally initiated by the addition of glycerol carbonate. The glycerol carbonate is added preferably dropwise, ideally at temperatures between 70° C. and 110° C.

The mixture is preferably dewatered before the addition of the glycerol carbonate (i.e. before the start of the transesterification). For example, the dewatering may be effected by distilling the water off as an azeotrope with methyl (meth)acrylate.

The catalyst is used preferably in amounts of 1.0% to 5.0% by weight based on the total weight of the mixture.

The ratio of glycerol carbonate to methyl (meth)acrylate in the reaction mixture may preferably be set at a ratio of 1:6 or higher, preferably at a ratio of between 1:6 and 1:12.

In an embodiment of the invention, the ratio of glycerol carbonate to methyl (meth)acrylate in the reaction mixture is set at 1:10.

In an alternative embodiment, the ratio of glycerol carbonate to methyl (meth)acrylate in the reaction mixture is set at 1:6.

To shift the equilibrium, the methanol liberated may be distilled off as an azeotrope with methyl (meth)acrylate. In order to remove just the true azeotrope, the column used for its removal is optimally operated with sufficient reflux that the overhead temperature of the column has the exact boiling temperature of the azeotrope. As the reaction progresses, the rate of reaction decreases gradually, with the result that towards the end of the reaction only small amounts of azeotrope are still being obtained. At this point it is optimal to abolish the restriction on the overhead temperature. The consequence of this is that less methanol and more methyl (meth)acrylate are distilled off.

In the work underlying the invention, it was surprisingly found that, if the methyl (meth)acrylate is present in insufficient excess relative to the glycerol carbonate, this has a significantly adverse effect on crosslinker formation upon abolition of the overhead temperature.

The continuous addition of methyl (meth)acrylate in an amount that corresponds to 0.7 to 1.3 times the azeotropic distillate or the continuous addition of methyl (meth)acrylate in an amount equivalent to the azeotropic distillate counteracts the described effect and, in addition, can significantly increase the space-time yield. The excess methyl (meth)acrylate remaining at the end of the reaction may be removed at lower temperature and under reduced pressure without a substantial increase in the crosslinker content.

Consequently, the ratio of glycerol carbonate to methyl (meth)acrylate initially set in the reaction mixture is preferably kept constant for the entire duration of the reaction. In an embodiment of the invention, the ratio of glycerol carbonate to methyl (meth)acrylate remains at a constant 1:6 for the entire duration of the reaction.

In order to prevent unwanted polymerization, polymerization inhibitors/stabilizers may be used in the reaction (and during purification and storage). The terms "inhibitor" and "stabilizer" are used synonymously in the context of this invention. These compounds, for example hydroquinones, hydroquinone ethers such as hydroquinone monomethyl ether or di-tert-butylcatechol, phenothiazine, N,N'-(diphenyl)-p-phenylenediamine, 4-hydroxy-2,2,6,6-tetramethylpiperidine 1-oxyl, p-phenylenediamine, methylene blue or sterically hindered phenols, are used very widely in industry. These compounds may be used individually or in the form of mixtures and are generally commercially available. The mode of action of the stabilizers is usually that they act as free-radical scavengers for the free radicals that occur in the polymerization. Further details are given in the relevant technical literature, particularly Römpp-Lexikon Chemie; editors: J. Falbe, M. Regitz; Stuttgart, New York; 10th edition (1996); keyword "Antioxidantien" [antioxidants] and literature references cited therein.

Based on the weight of the total reaction mixture, the content of stabilizer(s), either individually or as a mixture, is generally 0.005% to 0.5% (wt/wt).

These polymerization inhibitors may be added to the reaction mixture before or at the start of the reaction. In addition, small proportions of the polymerization inhibitors used may be introduced during the transesterification. Of particular interest here are processes in which part of the polymerization inhibitor is added into the column reflux. It is particularly advantageous to use inter alia mixtures that comprise methyl (meth)acrylate, hydroquinone monomethyl ether and 4-hydroxy-2,2,6,6-tetramethylpiperidine 1-oxyl. This measure makes it possible, in particular, to avoid unwanted polymerization inside the distillation column.

In addition to this, dissolved oxygen may be used for stabilization. This may, for example, be in the form of air, with the amounts introduced preferably such that the content in the gas phase above the reaction mixture remains below the explosion limit. Likewise, it is possible to use inert gas/oxygen mixtures, e.g. nitrogen/oxygen or argon/oxygen mixtures.

In a particular embodiment of the present invention, a combination of dissolved oxygen with hydroquinone monomethyl ether (HQME) may be used for stabilization.

The reaction may be carried out at standard pressure, reduced pressure or elevated pressure. In a particularly advantageous modification of the present invention, the transesterification may be carried out at a pressure within a range from 200 to 2000 mbar, in particular within a range from 500 to 1300 mbar and preferably within a range from 800 to 1050 mbar.

The reaction temperature may, depending on the pressure in particular, likewise be within a wide range. In a particular embodiment of the present invention, it may be carried out at a temperature within a range from 60° C. to 150° C., in particular from 70° C. to 140° C. and preferably from 90° C. to 135° C.

The transesterification may be carried out without the use of another solvent. Alternatively, it is also possible to use an inert solvent. Such solvents include inter alia benzene, toluene, n-hexane, cyclohexane and methyl isobutyl ketone (MIBK) and methyl ethyl ketone (MEK).

The liberated alcohol may subsequently be removed from the reaction mixture by distillation, optionally as an azeotrope with methyl (meth)acrylate. The alcohol may also be removed as an azeotrope with n-hexane or cyclohexane.

The reaction may preferably be carried out with stirring, in which case the stirrer speed must be adjusted according to the scale of the reaction. For example, the stirrer speed may be within a range from 20 to 5000 rpm, preferably within a range from 50 to 2000 rpm and more preferably within a range from 100 to 500 rpm.

The reaction times depend inter alia on the chosen parameters such as pressure and temperature. However, they are generally within a range from 1 to 24 hours, preferably from 5 to 20 hours and more preferably from 6 to 18 hours.

On completion of the transesterification reaction (or on termination of the reaction), the catalyst may be removed by precipitation (for example with dilute phosphoric acid) and filtration. The purification of the crude product may, if required, be carried out by the usual methods.

The process according to the invention is preferably executed as a batch process. If this is done, excess methyl (meth)acrylate may be removed by distillation towards the end of the reaction. This may be reused in the next batch without further purification.

Glycerol carbonate (meth)acrylate may be used as a functional monomer in copolymers for coatings and adhesives, with which a subsequent polymer-analogous reaction, including crosslinking with difunctional amines in a coating formulation, is possible. It may also be used in battery electrolytes, extrusion resins and for the extraction of metals.

The following examples elucidate the process according to the invention without this being limited to said examples.

Example 1: Molar Ratio 1:10, Addition of 15% Water

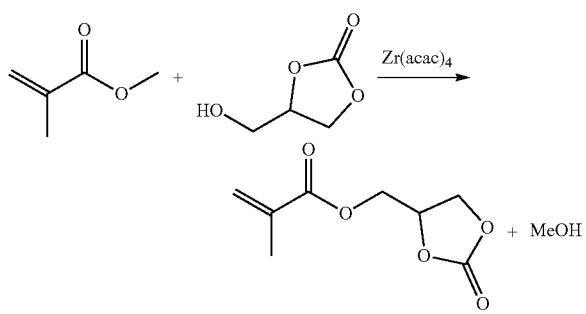

Mixture:

| 1200 g | 12.0 mol | methyl methacrylate (MMA) |
| 0.13 g | 100 ppm (based on mixture) | hydroquinone monomethyl ether (HQME) |
| 26.0 g | 1.9% (based on mixture) | Zr(acac)$_4$ |
| 3.9 g | 15% (based on catalyst) | H$_2$O |
| 142 g | 1.2 mol | glycerol carbonate |

Procedure:

A 2 L four-necked round-bottomed flask equipped with air inlet, addition funnel, mechanical stirrer, a 50 cm silvered packed column (d=29 mm, packed with 8×8 Raschig rings), automatic column head, condenser and temperature measurement sensors in the bottoms and at the column head was charged with Zr(acac)$_4$, hydroquinone monomethyl ether (HQME), water and methyl methacrylate (MMA). The mixture was boiled under reflux and the resulting water/MMA azeotrope was finally taken off. Glycerol carbonate was then added dropwise over a period of about one hour at a bottoms temperature of between 95 and 105° C. This was accompanied by a gradual decrease in the overhead temperature and, at an overhead temperature of <70° C., the resulting MMA/methanol mixture was taken off at a reflux ratio of 1:50 (take off/reflux). As soon as the overhead temperature was no longer below 75° C., and without further restriction of the overhead temperature and at a steady reflux ratio of 1:50, the resulting distillate was taken off until the overhead temperature was a constant 99-100° C. The total reaction time was about 12 h. The catalyst was then precipitated at 85° C. with 70 g of 10% phosphoric acid and the mixture stirred for 15 minutes. After filtering off the solid, the filtrate was concentrated down to 20 mbar on a rotary evaporator at an oil bath temperature of 120° C.

This afforded 193 g (86.5% of theory) of a clear, yellow product.

Analysis: (GC, Values in Area Percent)

| 88.6% | glycerol carbonate methacrylate |
| 2.5% | glycerol carbonate |
| 0.6% | glycerol monomethacrylate |
| 0.3% | glycerol dimethacrylate |
| 0.6% | glycerol trimethacrylate |

Example 2: Molar Ratio 1:10, Addition of 10% Water

Mixture:

| 1200 g | 12.0 mol | MMA |
| 0.13 g | 100 ppm (based on mixture) | HQME |
| 26.0 g | 1.9% (based on mixture) | Zr(acac)$_4$ |
| 2.6 g | 10% (based on catalyst) | H$_2$O |
| 142 g | 1.2 mol | glycerol carbonate |

Procedure:
See example 1.

This afforded 198 g (88.8% of theory) of a clear, yellow product.

Analysis: (GC, Values in Area Percent)

| 88.3% | glycerol carbonate methacrylate |
| 3.6% | glycerol carbonate |
| 0.8% | glycerol monomethacrylate |
| 0.4% | glycerol dimethacrylate |
| 0.5% | glycerol trimethacrylate |

Example 3: Molar Ratio 1:10, Addition of 20% Water

Mixture:

| 1200 g | 12.0 mol | MMA |
| 0.13 g | 100 ppm (based on mixture) | HQME |
| 26.0 g | 1.9% (based on mixture) | Zr(acac)$_4$ |
| 5.2 g | 20% (based on catalyst) | H$_2$O |
| 142 g | 1.2 mol | glycerol carbonate |

Procedure:
See example 1.

This afforded 201 g (90.1% of theory) of a clear, yellow product.

Analysis: (GC, Values in Area Percent)

| 88.0% | glycerol carbonate methacrylate |
| 3.4% | glycerol carbonate |
| 0.4% | glycerol monomethacrylate |

-continued

| | |
|---|---|
| 0.3% | glycerol dimethacrylate |
| 0.5% | glycerol trimethacrylate |

Example 4: Molar Ratio 1:6, Addition of 10% Water, Addition of Distilled-Off MMA Mixture:

| | | |
|---|---|---|
| 1200 g | 12.0 mol | MMA |
| 0.14 g | 100 ppm (based on mixture) | HQME |
| 43.1 g | 3.0% (based on mixture) | Zr(acac)$_4$ |
| 4.3 g | 10% (based on catalyst) | H$_2$O |
| 236 g | 2.0 mol | glycerol carbonate |
| 200 g | 2.0 mol | MMA (further addition) |

Procedure:

See example 1. However, in this case 200 g of MMA was added during the course of the reaction in accordance with the MMA/methanol mixture taken off.

This afforded 333 g (89.5% of theory) of a clear, yellow product.

Analysis: (GC, Values in Area Percent)

| | |
|---|---|
| 89.7% | glycerol carbonate methacrylate |
| 3.5% | glycerol carbonate |
| 0.5% | glycerol monomethacrylate |
| 0.5% | glycerol dimethacrylate |
| 0.9% | glycerol trimethacrylate |

Examples 1-3 demonstrate that, with a molar ratio of glycerol carbonate to MMA of 1:10, a product low in crosslinkers may be produced when the catalyst is first treated with a certain amount of water. In example 4, an increased space-time yield compared with examples 1-3 was achieved by reducing the molar ratio to 1:6. In order for the product obtained to still be in accordance with the invention, it is necessary to add an appropriate further amount of MMA here.

Comparative Example 1: Molar Ratio 1:10, No Addition of Water

Mixture:

| | | |
|---|---|---|
| 1200 g | 12.0 mol | MMA |
| 0.13 g | 100 ppm (based on mixture) | HQME |
| 26.0 g | 1.9% (based on mixture) | Zr(acac)$_4$ |
| 142 g | 1.2 mol | glycerol carbonate |

Procedure:

See example 1, except with no addition of water. The reaction time was only 6 hours.

This afforded 203 g (91.0% of theory) of a clear, yellow product.

Analysis: (GC, Values in Area Percent)

| | |
|---|---|
| 90.3% | glycerol carbonate methacrylate |
| 2.1% | glycerol carbonate |
| 1.3% | glycerol monomethacrylate |
| 0.5% | glycerol dimethacrylate |
| 2.1% | glycerol trimethacrylate |

Comparative Example 2: Molar Ratio 1:6, No Addition of Water

Mixture:

| | | |
|---|---|---|
| 1200 g | 12.0 mol | MMA |
| 0.13 g | 100 ppm (based on mixture) | HQME |
| 43.1 g | 3.0% (based on mixture) | Zr(acac)$_4$ |
| 236 g | 2.0 mol | glycerol carbonate |

Procedure:

See example 1, except with no addition of water.

This afforded 333 g (89.5% of theory) of a clear, yellow product.

Analysis: (GC, Values in Area Percent)

| | |
|---|---|
| 88.9% | glycerol carbonate methacrylate |
| 2.1% | glycerol carbonate |
| 0.8% | glycerol monomethacrylate |
| 0.4% | glycerol dimethacrylate |
| 3.0% | glycerol trimethacrylate |

Comparative Example 3: Molar Ratio 1:6, with Addition of Water, without Addition of MMA Mixture:

| | | |
|---|---|---|
| 1200 g | 12.0 mol | MMA |
| 0.14 g | 100 ppm (based on mixture) | HQME |
| 43.1 g | 3.0% (based on mixture) | Zr(acac)$_4$ |
| 4.3 g | 10% (based on catalyst) | H$_2$O |
| 236 g | 2.0 mol | glycerol carbonate |

Procedure:

See example 1.

This afforded 330 g (88.7% of theory) of a clear, yellow product.

Analysis: (GC, Values in Area Percent)

| | |
|---|---|
| 89.0% | glycerol carbonate methacrylate |
| 3.0% | glycerol carbonate |
| 0.6% | glycerol monomethacrylate |
| 0.6% | glycerol dimethacrylate |
| 1.2% | glycerol trimethacrylate |

Comparative Example 4

Mixture:

| | | |
|---|---|---|
| 1200 g | 12.0 mol | MMA |
| 0.13 g | 100 ppm (based on mixture) | HQME |
| 26.0 g | 1.9% (based on mixture) | Zr(acac)$_4$ |
| 3.9 g | 30% (based on catalyst) | H$_2$O |
| 142 g | 1.2 mol | glycerol carbonate |

Procedure:

See example 1.

This afforded 181 g (81.1% of theory) of a clear, yellow product.

Analysis: (GC, Values in Area Percent)

| | |
|---|---|
| 79.1% | glycerol carbonate methacrylate |
| 12.8% | glycerol carbonate |

| | |
|---|---|
| 0.4% | glycerol monomethacrylate |
| 0.4% | glycerol dimethacrylate |
| 0.2% | glycerol trimethacrylate |

Comparative examples 1 and 2 demonstrate that a product low in crosslinkers cannot be produced without addition of water at the start. Comparative example 3, on the other hand, demonstrates the effect of the lower molar ratio (1:6) without addition of the MMA that was distilled off. Although this results in a significant reduction in the crosslinker content compared with comparative examples 1 and 2, the content thereof is still higher than required. Comparative example 4 demonstrates that, if the amount of water at the start of the reaction is too high, the reaction no longer proceeds to completion, with 12.8% of the starting material glycerol carbonate still present at the end of the reaction time.

The invention claimed is:

1. A process for preparing glycerol carbonate (meth)acrylate, the process comprising:
    reacting, by transesterification, methyl (meth)acrylate with glycerol carbonate in the presence of a zirconium acetylacetonate catalyst, in a reaction mixture, to obtain glycerol carbonate (meth)acrylate,
    wherein the catalyst is pretreated with 2% by weight to 25% by weight of water, based on an amount of the catalyst.

2. The process according to claim 1, wherein the catalyst is pretreated with 8% by weight to 20% by weight of the water, based on the amount of the catalyst.

3. The process according to claim 1, wherein the pretreatment of the catalyst with the water takes place in the presence of the methyl (meth)acrylate and, optionally, in the presence of at least one stabilizer.

4. The process according to claim 1, wherein the pretreatment of the catalyst with the water takes place within a temperature range of between 70° C. and 110° C.

5. The process according to claim 1, wherein after the pretreatment of the catalyst, the reaction mixture is dewatered before the transesterification.

6. The process according to claim 1, wherein the reaction mixture comprises the catalyst in an amount of 1.0% to 5.0% by weight, based on a total weight of the reaction mixture.

7. The process according to claim 1, wherein a ratio of the glycerol carbonate to the methyl (meth)acrylate in the reaction mixture is set at a ratio of between 1:6 and 1:12.

8. The process according to claim 1, wherein a ratio of the glycerol carbonate to the methyl (meth)acrylate in the reaction mixture is set at 1:10.

9. The process according to claim 1, wherein a ratio of the glycerol carbonate to the methyl (meth)acrylate in the reaction mixture is set at 1:6.

10. The process according to claim 1, wherein methanol formed during the transesterification is distilled off with the methyl (meth)acrylate as an azeotrope, and further methyl (meth)acrylate is continuously added to the reaction mixture in an amount that corresponds to 0.7 to 1.3 times an amount of the azeotrope.

11. The process according to claim 1, wherein methanol formed during the transesterification is distilled off with the methyl (meth)acrylate as an azeotrope, and further methyl (meth)acrylate is continuously added to the reaction mixture in an amount equivalent to an amount of the azeotrope.

12. The process according to claim 1, wherein the reaction mixture contains at least one stabilizer.

13. The process according to claim 12, wherein the reaction mixture has a content of the at least one stabilizer of 0.005% to 0.5% by weight.

14. The process according to claim 1, wherein at least one hydroquinone-based polymerization inhibitor is present during the transesterification, optionally in combination with dissolved oxygen.

15. The process according to claim 14, wherein the at least one hydroquinone-based polymerization inhibitor is hydroquinone monomethyl ether (HQME).

16. The process according to claim 2, wherein the catalyst is pretreated with 9% by weight to 18% by weight of the water, based on the amount of the catalyst.

17. The process according to claim 14, wherein a ratio of the glycerol carbonate to the methyl (meth)acrylate in the reaction mixture is set at a ratio of between 1:6 and 1:12.

18. The process according to claim 14, wherein a ratio of the glycerol carbonate to the methyl (meth)acrylate in the reaction mixture is set at 1:10.

19. The process according to claim 14, wherein methanol formed during the transesterification is distilled off with the methyl (meth)acrylate as an azeotrope, and further methyl (meth)acrylate is continuously added to the reaction mixture in an amount that corresponds to 0.7 to 1.3 times an amount of the azeotrope.

20. The process according to claim 14, wherein the reaction mixture comprises the catalyst in an amount of 1.0% to 5.0% by weight, based on a total weight of the reaction mixture.

* * * * *